US00PP25842P3

(12) United States Plant Patent
Schoone

(10) Patent No.: US PP25,842 P3
(45) Date of Patent: Aug. 25, 2015

(54) ***PHALAENOPSIS* ORCHID PLANT NAMED 'AIRBORNE'**

(50) Latin Name: *Phalaenopsis hybrida*
Varietal Denomination: Airborne

(71) Applicant: Floricultura, Heemskerk (NL)

(72) Inventor: René Schoone, Assendelft (NL)

(73) Assignee: FLORICULTURA, Heemskerk (NL)

( * ) Notice: Subject to any disclaimer, the term of this patent is extended or adjusted under 35 U.S.C. 154(b) by 154 days.

(21) Appl. No.: 13/986,344

(22) Filed: Apr. 23, 2013

(65) Prior Publication Data

US 2013/0291262 P1 Oct. 31, 2013

Related U.S. Application Data

(60) Provisional application No. 61/638,024, filed on Apr. 25, 2012.

(30) Foreign Application Priority Data

Apr. 26, 2012 (NL) ..... PBR OPS907

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Airborne' particularly characterized by flowers which are mainly purple with irregular white bands at the margins and in the labellum some yellow; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Airborne'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Airborne'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Airborne' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Airborne' originated from a cross made by the inventor in 1999 in Strengweg, Heemskerk, The Netherlands. The female or seed parent is the *Phalaenopsis* cultivar designated 'Sogo Tris', unpatented. The male or pollen parent is the *Phalaenopsis* cultivar designated 'Ta-Lin', unpatented. The new *Phalaenopsis* 'Airborne' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Airborne', which in combination distinguish this *Phalaenopsis* as a new and distinct cultivar:

1. flowers which are mainly purple with irregular white bands at the margins and in the labellum some yellow;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Airborne', the flowers of the female parent 'Sogo Tris' are white with red/purple marks and a large purple midlobe and the male parent 'Ta-Lin' has white colored flowers, whereas the flowers of 'Airborne' are mainly purple with irregular white bands at the margins and in the labellum some yellow.

Presently, the commercial cultivar to which 'Airborne' can be meaningfully compared is 'Ophelia' (unpatented). 'Airborne' is a little smaller than 'Ophelia'. The flowers of 'Airborne' are mainly purple with irregular white bands at the margins, whereas the flowers of 'Ophelia' have more white and have many purple marks and spots.

BRIEF DESCRIPTION OF THE PHOTOGRAPHS

The accompanying photographs illustrate the overall appearance of the new *Phalaenopsis* 'Airborne' showing the colors as true as is reasonably possible with colored reproductions of this type. Colors in the photographs may differ slightly from the color values cited in the detailed botanical description, which accurately describe the color of 'Airborne'.

DETAILED BOTANICAL DESCRIPTION

Figure 1:
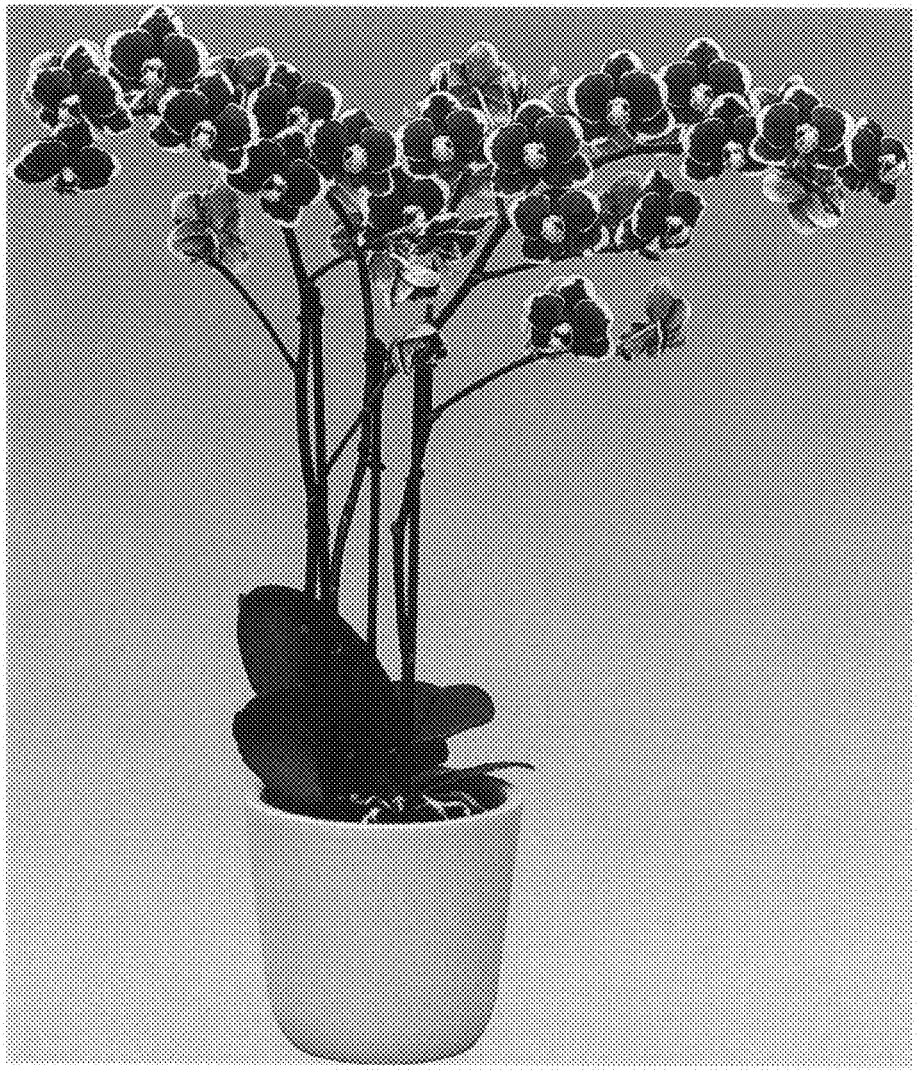
FIG. 1 shows a side view perspective of a typical flowering plant of 'Airborne' in a 12 cm pot, at 16 months of age.

The new *Phalaenopsis* cultivar 'Airborne' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Airborne' as grown in a greenhouse in Strengweg, Heemskerk, The Netherlands, under conditions which closely approximate those generally used in commercial practice. Initially, the ideal temperature to grow plants of 'Airborne' is 27° C. during the day and at night. Then, during the flowering phase of 'Airborne', the ideal growing temperature is 20-22° C. during the day and 18° C. at night. Light levels for growing 'Airborne' are a minimum of 5,000 lux and a maximum of 10,000 lux. A balanced fertilizer with level of 200 ppm N, 87 ppm P, 168 ppm K is applied. Duration of growth of 'Airborne' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Airborne' plants described is 12 months after potting.

Classification:

*Botanical.—Phalaenopsis hybrida.*

Parentage:

*Female or seed parent.—Phalaenopsis* cultivar designated 'Sogo Tris', unpatented.

*Male or pollen parent.—Phalaenopsis* cultivar designated 'Ta-Lin', unpatented.

Propagation:

*Type*.—Tissue culture.

*Rooting habit and description*.—Fleshy; approximately 3 mm-7 mm wide and green in color (a combination of RHS 191B and RHS 191C); freely branching. It takes 12 weeks for plants growing in tissue culture to initiate roots.

Plant:

*Size at maturity*.—Height (from bottom of pot to highest flower): about 50 cm. Spread: about 45 to 90 cm.

*Growth habit*.—Small; green leaves (RHS 139A) and a relatively normal raceme.

*Vigor*.—Moderate.

*Crop time*.—Following asexual propagation, at about 26 weeks 2 leaves appear; at about 30 weeks 3-4 leaves appear; after a cold treatment of about 4-8 weeks at a temperature of about 19° C. about 1-4 racemes with flowers appear.

Foliage:

*Quantity per plant*.—About 6 to 8 leaves are produced before flowering.

*Arrangement and attachment*.—Half up/horizontal and on two sides.

*Overall shape of leaf*.—Oval/egg-shaped, the tip is little pointy and asymmetric.

*Texture* (*upper & underside*).—Smooth and leathery.

*Pubescence*.—None.

*Mature leaf length*.—About 11 to 16 cm.

*Mature leaf width*.—About 7 to 10 mm.

*Mature leaf thickness*.—About 2 mm.

*Mature leaf color*.—Upper side: green (RHS 139A). Under side: green (RHS 137B and 146D).

*Leaf base*.—Acute.

*Margin*.—Entire.

*Venation*.—Pattern: parallel. Color of midvein: upper side: green (RHS 139A). Under side: green (RHS 139C).

Inflorescence description:

*Appearance*.—Upright to slightly pendant, racemose inflorescence with bilaterally symmetrical flowers that open in succession beginning with the lowermost flower.

*Raceme*.—Quantity per plant: about 1 to 4. Number of flowers per raceme: about 6 to 19. Length: about 30 to 50 cm.

*Peduncle*.—Diameter: about 4 to 6 mm. Strength: strong. Aspect: upright. Texture: glabrous and smooth. Color: green (RHS 138A).

*Buds*.—Height (from base to tip): about 15 to 30 mm. Diameter (at midpoint): about 10 to 18 mm. Shape: oval/egg-shaped with a bump on the side. Color: yellow/green (RHS 145C) and purple (RHSN79).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1-4 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
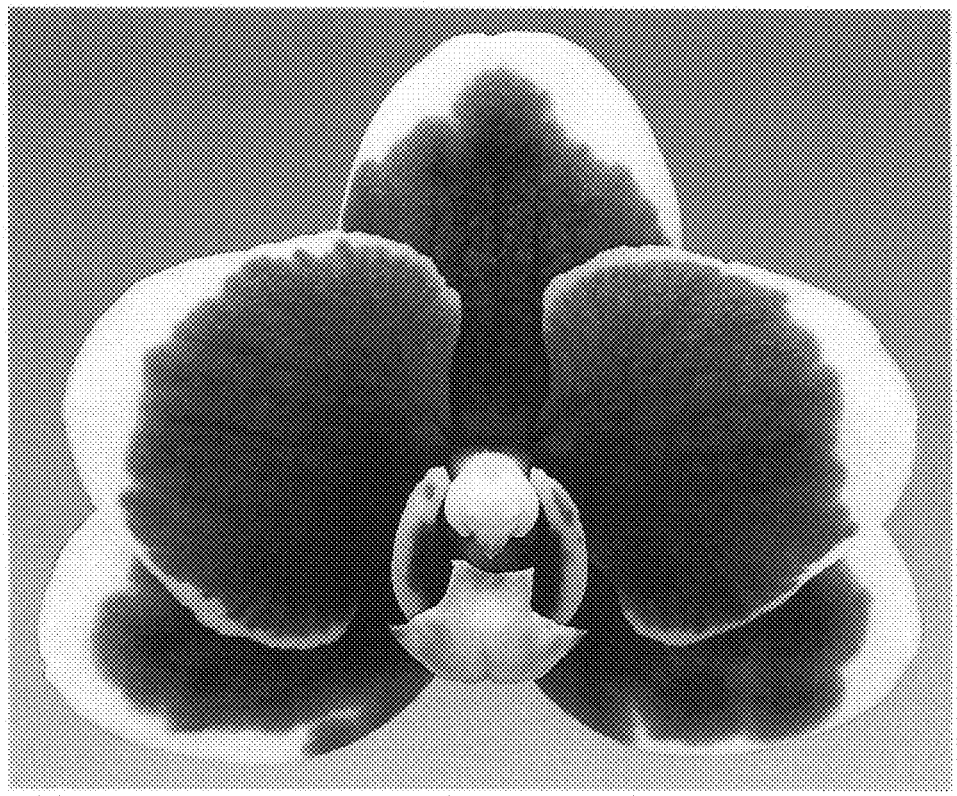
FIG. 2 shows a close-up view of a typical flower of 'Airborne'.
Figure 3:
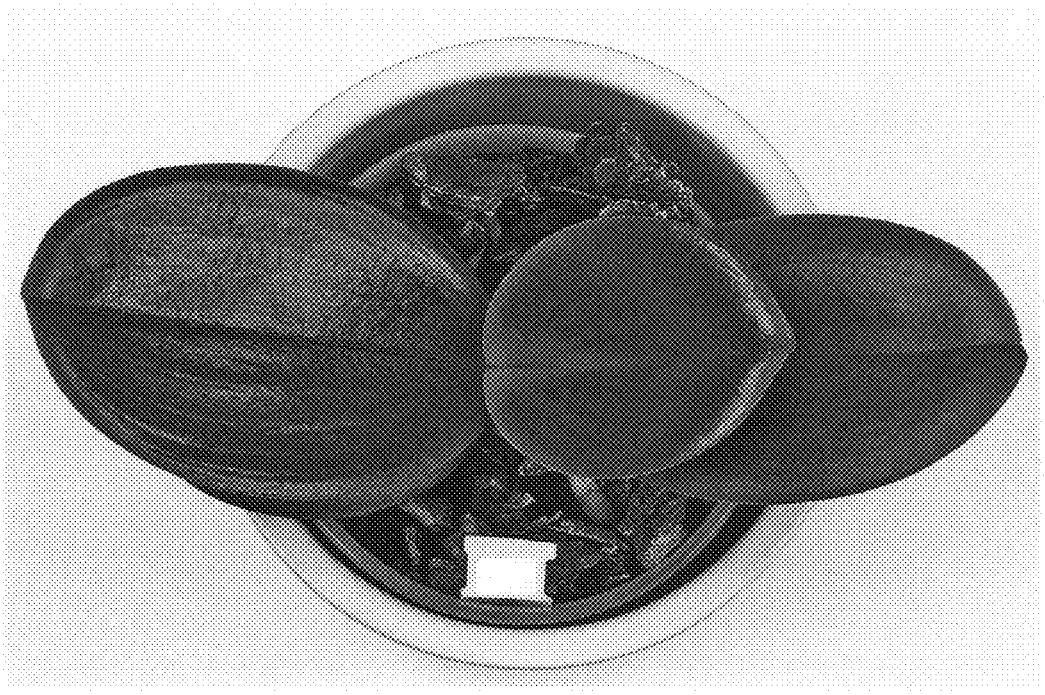
FIG. 3 shows a close-up view of the typical leaves of 'Airborne'.

*Flower*.—Rate of opening: Flowers fully opened about 2 to 3 days after petal and sepal separation. Orientation at opening: slanted upward and outward. Shape: Typical shape of *Phalaenopsis* orchid: see FIG. 2. Size (of single bloom): Height: about 29 mm to 50 mm. Diameter: about 39 mm to 55 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: broadly ovate, little triangular. Apex: oval. Margin: entire and weakly undulate. Base: broadly ovate. Length: about 22 mm. Width: about 23 mm. Texture: Upper surface: smooth and satiny. Under surface: smooth and satiny. Color (when fully opened): upper side: purple (RHS N79B) with a red/purple edge (RHS N81A). The edge of the flower is white (RHS NN155D). At the base starts a small white edge (RHS NN155D) which turns wider at the top. Under side: outermost edges (RHS N81A) runs in the middle out into RHS N81C. At the base white and the edges also white (RHS NN155D) at the top the white edge is much wider than at the base. Labellum: Overall Representation: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin: entire. Apex: weakly undulate. Length: about 15 mm to 20 mm. Width (not flattened): about 10 mm to 18 mm. Depth of tube created by lateral lobes of labellum: about 9 mm. Texture: Upper and under surface: smooth and satiny. Color (when fully opened): Midlobe: upper surface: At the top white (RHS NN155D) and purple (RHS 84D) with purple spots (combination RHS 79B and RHS 79C). At the base yellow (RHS 3A) with red/purple spots (RHS 60A). At the base and in the center darker purple spot (RHS N92A). Under surface: from the cirrhi white (RHS NN155D) which runs into purple (RHS 84D) with purple spots (RHS 79B) and at the side purple spots (RHS N78A). At the base some yellow (RHS 3A). Lateral lobes: upper surface: from the base the upper side is purple (RHS N79A) which runs into RHS N80A. the lower edge is yellow (RHS 3A). At the end white edge (RHS NN155D) with purple spots in it (RHS N80A). Under surface: white (RHS NN155D), from base the lower edge is yellow (RHS 3A). From base the upper edge is RHS N79D which runs into RHS N79A and a little bit RHS N80A. Cirrhi: about 0.5 mm. (little tips). Color: RHS NN155D. Pestle (Callosities): Length: about 3 mm. Width (not flattened): about 3 mm. Color: the upper side and inner side are purple (RHS N77A). Sides and front are yellow/orange (RHS 15C).

*Sepals*.—Arrangement: Outer whorl comprises 3 sepals, one dorsal and two lateral sepals. Overall shape: egg-shaped. Margin: entire and weakly undulate. Length: about 23 mm. Width: about 20 mm. Apex: lateral is oval and dorsal is round. Texture: Upper and under surface: smooth and satiny. Color (when fully opened): upper side: purple (RHS N79B) with a lighter edge (RHS N81A) which runs into white (RHS NN155D). Under side: main color is purple (RHS N79B) with a the top a white edge (RHS NN155D). At some sepals at the base a little green (RHS 146D).

*Pedicel*.—Length: about 23 to 35 mm. Diameter: about 2 to 4 mm. Texture: glabrous and smooth. Color: at the flower yellow/green (RHS 150D) at the pedicel red/purple (RHS 71A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 8 mm. Diameter: about 5 mm. Color: white (RHS NN155D) in the middle a purple stripe (RHS N78B).

*Pollinia*.—Quantity: two. Diameter: about 1 mm. Color: yellow/orange (RHS 23A).

*Ovary*.—Length: about 3 mm. Diameter: about 2 mm. Color: purple (RHS N78A).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Airborne', as illustrated and described herein.

* * * * *